United States Patent [19]
Hageman

[11] Patent Number: 5,292,509
[45] Date of Patent: Mar. 8, 1994

[54] METHOD FOR THE DISINSERTION OF VITREOUS BODY BY AN ENZYME WHICH DISRUPTS OR DEGRADES CHONDROITIN SULFATE PROTEOGLYCAN

[75] Inventor: Gregory S. Hageman, St. Louis, Mo.

[73] Assignee: Bethesda Eye Institute, St. Louis, Mo.

[21] Appl. No.: 894,526

[22] Filed: Jun. 5, 1992

Related U.S. Application Data

[63] Continuation of Ser. No. 509,367, Apr. 16, 1990, abandoned.

[51] Int. Cl.$^5$ .............................................. A61K 37/54
[52] U.S. Cl. ................................. 424/94.61; 424/94.62
[58] Field of Search ........................... 424/94.61, 94.62

[56] References Cited

U.S. PATENT DOCUMENTS

| | | | |
|---|---|---|---|
| 4,174,389 | 11/1979 | Cope | 424/94 |
| 4,524,065 | 6/1985 | Pinnell | 424/94.67 |
| 4,696,816 | 9/1987 | Brown | 424/94.65 |

FOREIGN PATENT DOCUMENTS

| | | | |
|---|---|---|---|
| 2840173 | 9/1978 | Fed. Rep. of Germany | 424/94.61 |

OTHER PUBLICATIONS

Winkler et al. "Hyaluronidase and Retinal Function", Arch Ophthalmol, 103 (11), pp. 1743–1746, 1985.
Thomson, "Addition of hyaluronidase to lignocaine with adrenaline for retrobulbar anesthesia in the surgery of senile cataract", Am. J. Ophthalmol, 107, p. 99 (1989), Abstract.

*Primary Examiner*—Marian C. Knode
*Attorney, Agent, or Firm*—Senniger, Powers, Leavitt & Roedel

[57] ABSTRACT

A method for selectively and completely disinserting the ocular vitreous body, epiretinal membranes and/or fibrocellular membranes from the neural retina, ciliary epithelium and posterior lens surface of the mammalian eye as an adjunct to vitrectomy comprises administering to the eye an effective amount of a protease-free glycosaminoglycanase enzyme, such as chondroitinase ABC, adapted to disrupt and/or degrade chondroitin sulfate glycosaminoglycan/proteoglycan localized specifically to sites of vitreoretinal adhesion and thereby permit complete disinsertion of the vitreous body and/or epiretinal membranes.

9 Claims, 11 Drawing Sheets

PARS

ORA

PARS

ORA

PARS

ORA

CENTRAL

ONH

ERM

10A

10B

METHOD FOR THE DISINSERTION OF VITREOUS BODY BY AN ENZYME WHICH DISRUPTS OR DEGRADES CHONDROITIN SULFATE PROTEOGLYCAN

This is a continuation of application Ser. No. 509,367, filed Apr. 16, 1990, now abandoned.

BACKGROUND OF THE INVENTION

This invention relates to enzymatic disruption of the vitreoretinal interface and, more particularly, to enzymatic disinsertion or complete removal of the vitreous body in association with surgical vitrectomy.

The vitreous body, a connective tissue compartment which occupies four-fifths of the volume of the eye, provides structural and metabolic support for ocular tissues and assists in the maintenance of intraocular pressure while at the same time allowing light access to the retina. This structure is bound anteriorly by the lens and ciliary body epithelium and posteriorly by the retina. The vitreous exists as a semi-solid, highly transparent gel and is composed of approximately 99% water and 1% macromolecules including collagen, hyaluronic acid, a number of unidentified, soluble glycoproteins, sugars and various low molecular weight metabolites. The distribution of type II collagen, the major structural protein within the vitreous, is quite regular and essential for the mechanical properties of this highly diluted gel. During the earlier years of life, the vitreous is differentiated into a cortex of high density and a semi-fluid central vitreous; in early adolescence destruction of the vitreous framework begins, leading to the formation of liquified cavities and fibrillar strands within the vitreous gel during later years.

Normal anatomic attachments between the vitreous body and retina occur in a number of regions, although the molecular basis for normal vitreoretinal adhesion is still unknown (see FIG. 1). The zone of strongest vitreoretinal adherence, the vitreous base, straddles the ora serrata and measures approximately 3.2 mm in the anterior-to-posterior meridian (FIG. 1). Its anterior border is associated with the posterior pars plana; the posterior border expands gradually from the ora serrata towards the equator with age. The connection between the retinal basal lamina and the collagen fibrils in the region of the vitreous base is so strong in the normal human that, when the vitreous is pulled in an attempt to separate them, either the vitreous cortex breaks away from the rest of the vitreous or part of the cells of the retina and ciliary body break away from the ocular wall. In other words, the attachment is mechanically stronger than that of the vitreous gel itself. Other zones of vitreoretinal attachment, although weaker, exist at the borders of "cortical holes" including those around the optic disc ("peripallary"), around the fovea ("posterior vitreous base"), along major retinal vessels and at sights of developmental anomalies. Secondary sites of strong vitreoretinal attachment often develop at the border of degenerative or inflammatory lesions providing tractional pivot points on the surface of the retina which often cause its detachment.

Vitrectomy, the surgical removal of a portion of the vitreous body and/or associated "membranes" (epiretinal; fibrous), is indicated for the treatment or prevention of a variety of pathologic, operative, or postoperative conditions which, if untreated, can result in blindness. Typically, vitrectomy is performed secondary to complications which affect the normal vitreoretinal interface. These complications can be placed into three basic categories; 1) the development of secondary attachments between the vitreous and the retina, such as those which develop at sites of chorioretinal scars or in the vicinity of retinal neovascularization; 2) loss of normal adhesion between the retina and vitreous resulting in partial or complete vitreous detachment; and 3) the formation of cellular and/or fibrous membranes along the vitreoretinal interface and/or within the vitreous framework. Indications for vitreous surgery include proliferative retinopathy, complicated rhegmatogenous retinal detachment, epiretinal membrane formation, secondary (pathologic) vitreous detachment, vitreomacular traction, retinal detachment associated with retinopathy of prematurity, vitreous hemorrhage, perforating trauma, cataract removal, endophthalmitis, persistent hyperplastic primary vitreous, and a number of operative and postoperative complications which affect the vitreous secondarily. The primary concern in most cases of vitreoretinal pathology is the production of retinal tears and ultimately, detachment of the retina. Retinal detachment, if not treated immediately, will lead to photoreceptor cell (those cells responsible for transduction of light impulses into electrical impulses) death and, consequently, loss of vision. For example, in cases of imcomplete vitreous detachment, the vitreous gel remains attached to the retina at the optic disc and-/or the macula, and to the vitreous base. Secondary fibrous proliferation associated with these sites of adhesion leads to vitreopapillary and/or vitreomacular traction which can create tears in the retina.

Proliferative vitreoretinopathy (PVR), another example of a vitreoretinal abnormality, continues to be one of the most devastating types of vitreoretinal pathology leading to retinal detachment. In the most common type of PVR, that following retinal detachment, retinal pigment epithelial cells migrate into and proliferate within the vitreous scaffold, contributing to the formation of cellular (and fibrocellular) membranes which contract and cause retinal tears and/or retinal detachment. Peeling and/or delaminating these and other membranes from the retinal surface has become a standard procedure during vitrectomy. However, these procedures pose a great surgical risk and most often result in the creation of retinal tears and detachment. In addition, retinal tears can be created when the surgeon comes too close to the retinal surface with various instruments or when too much suction is applied on the vitreous at sites of firm vitreoretinal adhesion.

Despite the continued development and improvement of surgical techniques, creation of retinal tears and detachment is often unavoidable, due largely to our lack of knowledge pertaining to the fundamental mechanism and biology of vitreoretinal attachment. Major advances in the prevention and management of retinal detachment resulting from abnormal vitreoretinal adhesion will require detailed anatomical, biochemical and physiological research on the vitreoretinal interface if the causes of abnormal vitreous adhesion and shrinkage are to be understood.

The prior art is devoid of any disclosure of methodology for effectively insuring the selective and complete disinsertion of the ocular vitreous body, epiretinal membranes and/or fibrocellular membranes from the neural retina, ciliary epithelium, and posterior lens surface of the eye as an adjunct to vitrectomy.

Moorhead et al. (*Retina*, 5:98-100, 1985; *Arch. Ophthalmol.* 101:265-274, 1983) discloses enzyme-assisted vitrectomy using bacterial collagenase (Clostridiopeptidase A) for facilitating removal of fibroproliferative tissue and epiretinal membranes by partial digestion of the fibrous membrane prior to removal. The bacterial collagenase is stated to act by partial digestion of the fibrous membrane, thereby facilitating the removal of intravitreal fibroproliferative tissue.

Cope U.S. Pat. No. 4,174,389 discloses a method for the selective lysis of collagen fibrils located in the vitreous of the ocular region of a mammal through the administration of collagenase. According to the Cope patent, a significant amount of liquifaction occurs when the vitreous is contacted with collagenase.

Shehab et al. (*Invest. Ophthalmol. Vis. Sci. Suppl.* 27:317, 1986) disclose the effectiveness of six enzymes, including collagenase and chondroitinase ABC, to liquify the vitreous of freshly enucleated pig eyes by measuring the time required for total vitrectomy. Based upon the results obtained, Shehab et al. utilized protease-containing chondroitinase ABC.

Brown U.S. Pat. No. 4,696,816 discloses a method for the treatment of intervertebral disc displacement in humans using the enzyme chondroitinase ABC or AC to bring about the selective chemonucleolysis of the nucleus pulposus which contains proteoglycans and randomly dispersed collagen fibers.

Yamagata et al. (*Chem. Abstracts*, 68:84511g, 1968) disclose that the enzyme chondroitinase ABC selectively degrades chondroitin sulfates A, B, and C at pH 8.

There remains a need for improved methods for complete enzymatic removal or disinsertion of vitreous body as an adjunct to surgical vitrectomy, which methods are based upon the identification of the component(s) responsible for vitreoretinal adhesion.

SUMMARY OF THE INVENTION

Among the objects of the invention may be noted the provision of a novel method for selectively and completely disinserting the ocular vitreous body and/or associated epiretinal membranes from the neural retina, ciliary epithelium and posterior lens surface of the mammalian eye as an adjunct to surgical vitrectomy; the provision of such a method which is based upon the discovery that chondroitin sulfate-containing proteoglycan is involved in vitreoretinal adhesion; and the provision of an improved method for disinsertion of vitreous body which can be carried out without deleterious effect upon the eye. Other objects will be in part apparent and in part pointed out hereinafter.

Briefly, the present invention is directed to a method for selectively and completely disinserting the ocular vitreous body, epiretinal membranes and/or fibrocellular membranes from the neural retina, ciliary epithelium and posterior lens surface of the mammalian eye as an adjunct to vitrectomy which comprises administering to the eye an effective amount of an enzyme adapted to disrupt and/or degrade chondroitin sulfate glycosaminoglycan/proteoglycan localized specifically to sites of vitreoretinal adhesion and thereby permit complete disinsertion of said vitreous body and/or epiretinal membranes. The preferred enzyme for use in practicing the invention and achieving such complete disinsertion is chondroitinase ABC.

BRIEF DESCRIPTION OF THE DRAWINGS

FIG. 7 depicts a section of central retina (compare to FIG. 5) from a monkey eye with an epiretinal membrane. Note the intense binding of chondroitin sulfate antibody between the retina and epiretinal membrane (see arrows); similar binding is not observed in normal eyes (FIG. 5);

DESCRIPTION OF THE PREFERRED EMBODIMENTS

Figure 1:
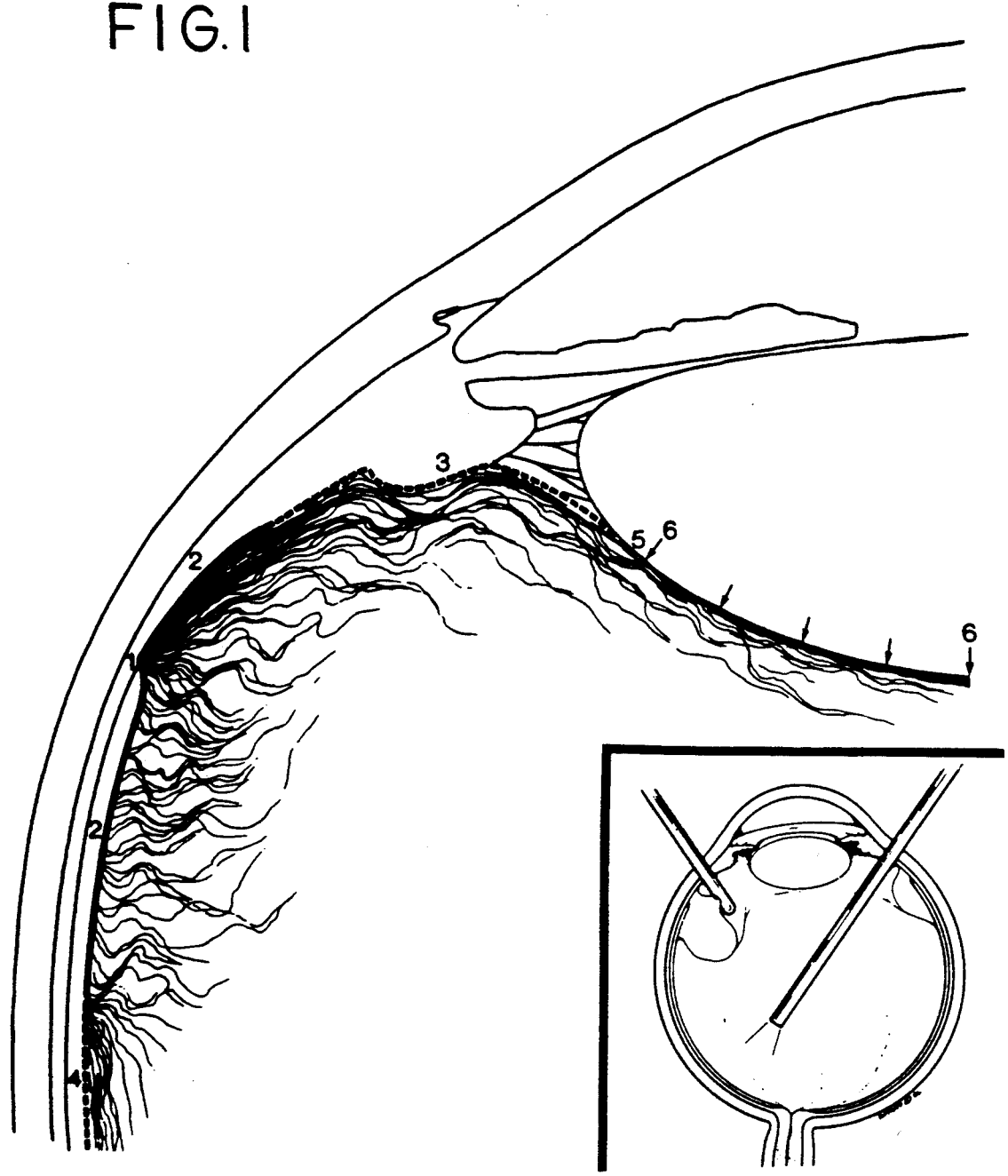
FIG. 1 is a diagrammatic representation of a meridianal section of a human eye depicting normal vitreoretinal associations. The strongest adhesion between the vitreous body and the retina occurs at the vitreous base (labeled 1 and 2) which is associated with the ora serrata (1) and pars plana (2). Weaker adhesions occur between the peripheral and central retina and the vitreous (4) and between the vitreous and posterior lens capsule (6). In addition, strong adhesion sites exist surrounding the optic nerve head (see FIG. 6) and macula. The inset of FIG. 1 is a diagrammatic representation depicting the results of a typical vitrectomy. Note that a large cuff of vitreous is left behind in the region of the vitreous base; this region of the vitreous cannot be removed owing to the strong adhesion between the vitreous and retina in this region. This remaining vitreous often serves as a scaffold into which cells migrate abnormally, forming epiretinal membranes which require additional surgery to remove.
Figure 2A:
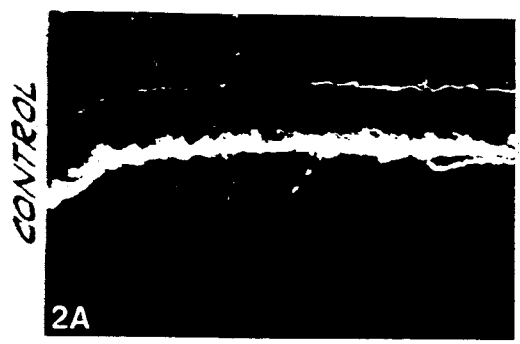
FIGS. 2-4 are fluorescence light micrographs of the pars plana and ora serrata regions of monkey eyes incubated with an anti-chondroitin sulfate antibody. Tissue was procured from a control monkey (FIGS. 2A-B), a vitrectomized monkey without enzymatic treatment (FIGS. 3A-B), and a monkey following treatment with chondroitinase ABC and vitrectomy (FIGS. 4A-8). Intense binding of anti-chondroitin sulfate is present within the vitreous base along the pars plana and ora serrata (see arrows) in both the control monkey and in the monkey which was vitrectomized without enzyme treatment. In contrast, binding of anti-chondroitin sulfate is abrogated in the monkey which was subjected to enzyme treatment and vitrectomy. Electron microscopic observations (not shown) confirm that the vitreous base was removed in the monkey subjected to enzyme treatment, but not in the vitrectomized or control monkeys.
Figure 2B:
Figure 3A:
Figure 3B:
Figure 4A:
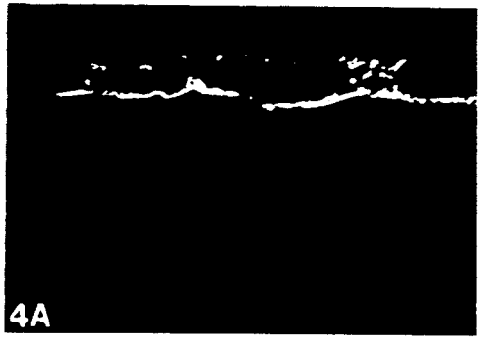
Figure 4B:
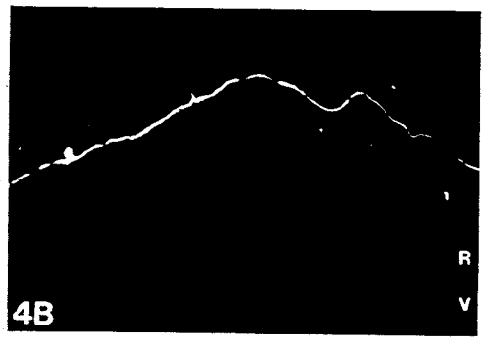
Figure 5:
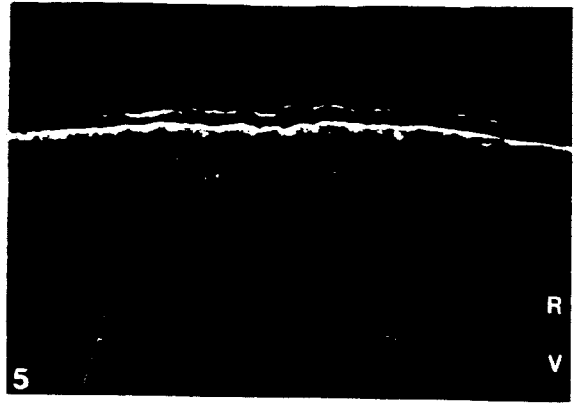
FIGS. 5-7 are fluorescence light micrographs of the vitreoretinal interface in the central retina (FIG. 5) and around the optic nerve head (FIG. 6) of a control monkey. Note that binding of anti-chondroitin sulfate is not present along the central retina, a region of weak vitreoretinal adhesion. In contrast, binding of chondroitin sulfate is present around the optic nerve head (papillary region), a region of firm attachment between the retina and vitreous (see arrow).
Figure 6:
Figure 7:
Figure 8A:
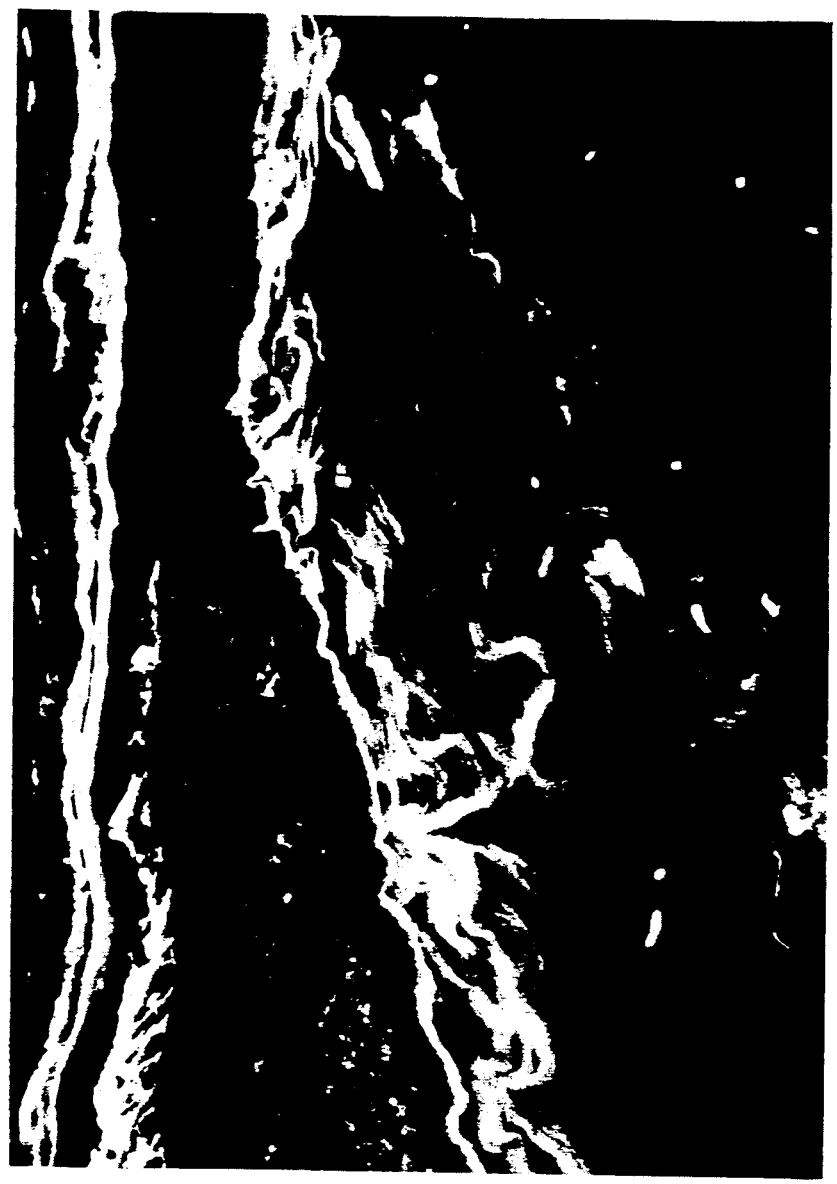
FIGS. 8A and 9A) is readily apparent in eyes not receiving chondroitinase ABC treatment following core vitrectomy. In contrast, histologically detectable vitreous (v) is not observed adjacent to the retina (R) in eyes receiving chondroitinase ABC treatment (FIG. 8B); the absence of vitreous following chondroitinase ABC treatment is also apparent in an enucleated eye which was bisected immediately after the enzymatic procedure (FIG. 9B).
Figure 8B:
FIGS. 8 and 9 are light micrographs of the pars plana and the ora serrata regions of control (FIGS. 8A and 9A) monkey eyes subjected to chondroitinase ABC treatment (FIGS. 8B and 9B). The vitreous body (v.

In accordance with the present invention, it has now been found that chondroitin sulfate, a glycosaminoglycan which is attached to a larger molecular weight proteoglycan, is the molecule responsible for vitreoretinal adhesion and that the vitreous body can be selectively and completely disinserted, or removed, through the administration of an enzyme adapted to disrupt and/or degrade chondroitin sulfate glycosaminoglycan/proteoglycan localized specifically to sites of such vitreoretinal adhesion. The discovery that chondroitin sulfate proteoglycan is associated with regions of firm adhesion between the vitreous and retina constitutes the first recognition of the presence of a specific chemical moiety in regions of vitreoretinal adhesions and makes possible the selective and complete enzymatic disinsertion or removal of the vitreous from these sites of firm adhesion.

Using monoclonal antibodies directed against chondroitin sulfate (a glycosaminoglycan/proteoglycan), I have identified intense localization of this molecule within the vitreous base and at the site of vitreoretinal adhesion encircling the optic nerve head (see FIGS. 2-7). The distribution of antibody binding corresponds directly to those regions of the vitreoretinal interface which are known to be the regions of firmest adhesion between the retina and vitreous, indicating that chondroitin sulfate may function in the maintenance of normal vitreoretinal adhesion. This supposition is supported by the fact that chondroitin sulfate-containing proteoglycans function as cell surface-associated receptors which mediate adhesion between cells and the extracellular matrix in other cellular systems. Chondroitin sulfate proteoglycans, which consist of a core protein to which many glycan side chains are covalently attached, are associated with the cell membrane in a number of ways, including (1) direct insertion of the core protein, via a hydrophobic segment, into the plasma membrane; (2) covalent linkage of the core protein to an inositol-containing phospholipid, or (3) noncovalent linkage of the core protein or glycan side chains to a receptor which is itself an integral plasma membrane component. In either of the three configurations, the ability to disrupt the linkage between chondroitin sulfate (in the vitreous body) and the retina before or during vitrectomy provides a significant surgical advancement in that (1) the overall time of surgery could be reduced dramatically; and (2) complete removal of the vitreous could be accomplished, thereby reducing significantly the large percentage of operative and postoperative complications associated with vitrectomy and incomplete removal of the vitreous.

My observation that chondroitin sulfate, a molecule known to perform a role in cell-extracellular matrix adhesion in other systems, is associated with regions of firmest adhesion between the vitreous and retina is based upon studies which identify the presence of a specific chemical moiety in regions of vitreoretinal adhesions and provides the knowledge for selectively removing or disinserting the vitreous from these sites of firm adhesion. The studies described hereinafter show that the vitreous base and other regions of normal vitreoretinal adhesion and their associated regions of strong anti-chondroitin sulfate-binding were not removed during standard vitrectomy. In further accordance with the invention, the studies described hereinafter show that through the administration of an effective amount of an enzyme adapted to disrupt and/or degrade chondroitin sulfate glycosaminoglycan/proteoglycan localized specifically to sites of vitreoretinal adhesion, the ocular vitreous body and/or epiretinal membranes can be selectively and completely disinserted from the neural retina, ciliary epithelium and posterior lens surface of the eye as an adjunct to vitrectomy. The results set forth hereinafter demonstrate that the chondroitin sulfate immunoreactivity was completely abrogated and the vitreous base was removed or disinserted completely (see FIG. 4). These results provide further support that chondroitin sulfate glycosaminoglycan/proteoglycan plays a major role in vitreoretinal adhesion. Furthermore, no signs of retinal or ciliary body toxicity are noted by light or electron microscopy following enzyme administration.

In the practice of the invention, any enzyme adapted to disrupt and/or degrade chondroitin sulfate glycosaminoglycan/proteoglycan localized specifically to sites of vitreoretinal adhesion may be used to achieve complete disinsertion of the vitreous body and/or epiretinal membranes from the neural retina, ciliary epithelium and posterior lens surface of a mammalian eye. The enzyme employed may be any protease-free glycosaminoglycanase such as chondroitinase ABC, chondroitinase AC, chondroitinase B, chondroitin 4-sulfatase, chondroitin 6-sulfatase, hyaluronidase or $\beta$-glucuronidase. Chondroitinase ABC is available from Seikagaku Kogyo of Tokyo, Japan and is produced or isolated from *Proteus vulgaris*.

The dose of such enzyme required to achieve complete disinsertion of the vitreous body and/or epiretinal membrane in accordance with the invention will vary with the time of treatment. In general, for shorter periods of treatment, larger doses of the enzyme will be required and vice versa, with the appropriate and effective dosage in all cases being such as to avoid retinal or ciliary body toxicity. In the broadest aspect, between approximately 1 and 10,000 units of the enzyme may be employed. More preferably, between approximately 100 and 1000 units of the enzyme are used, with a unit being defined as the quantity of enzyme that catalyzes the formation of 1 micromole of unsaturated disaccharide from chondroitin sulfate per minute at 37° C., pH 8.0. The above dose ranges may also be set forth in terms of units of enzyme per milliliter of vitreous volume to be completely disinserted and, on this basis, for example, may be as low as 0.05–0.1 unit per ml. Also, as indicated, the time of treatment will vary in accordance with the dose employed and may range, for example, from periods as short as one minute up to several hours.

It is preferred that the enzyme be administered in the form of a pharmacologically acceptable or suitable buffered solution formed by mixing a concentrated amount of enzyme with a buffer solution. Any suitable buffer solution known to the art may be utilized, including buffers such as sodium acetate or Tris buffer or a Balanced Salt Solution often utilized during vitrectomy and produced by Alcon of Fort Worth, Tex. The enzymes useful in the practice of the invention are effective at a pH of approximately 4.5–9.0, but exhibit maximum effectiveness at a pH of about 8. The preferred pH range for buffered solutions of the enzyme employed in carrying out the method of the invention is therefore approximately 7–8.

The enzyme may be administered to the eye by various modes of administration known to the art. These include intravitreal, subvitreal, sublenticular and posterior chamber administration to the eye.

Figure 9A:
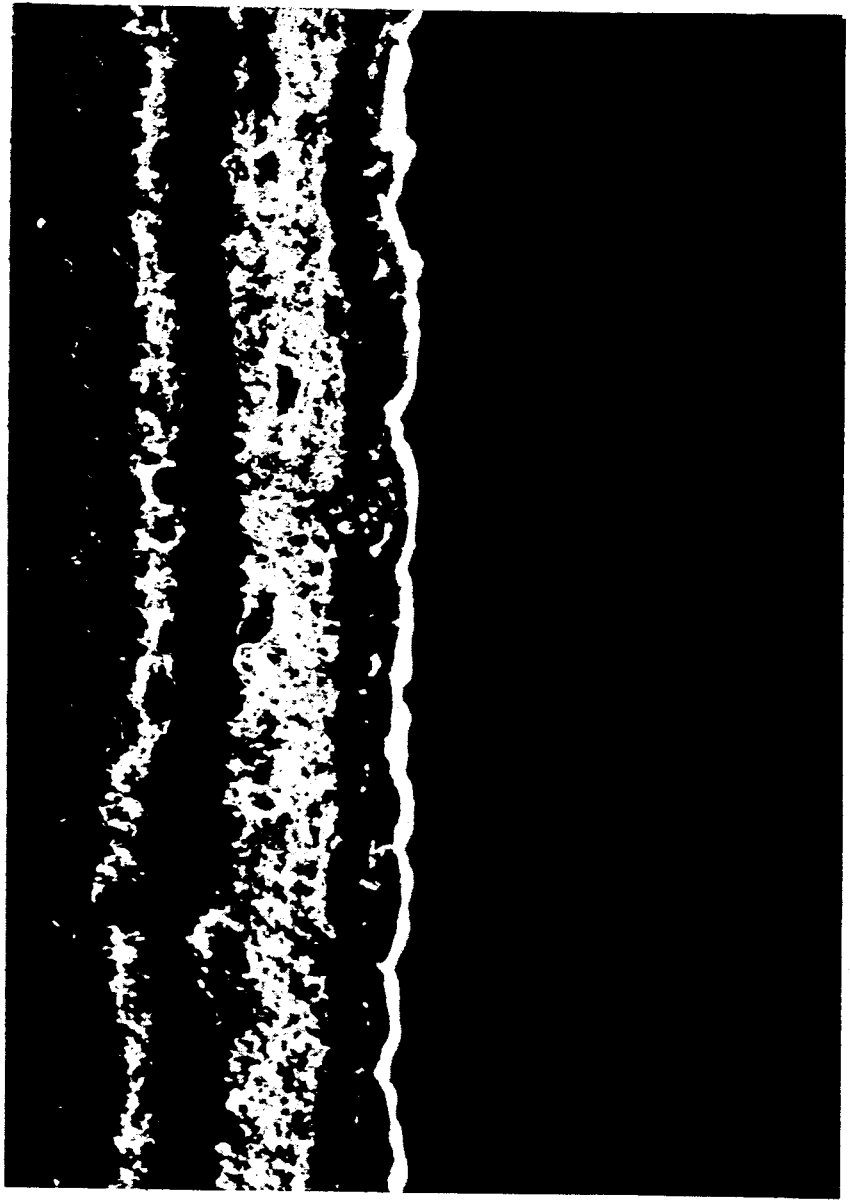
Figure 9B:
Figure 10A:
FIGS. 10A and 10B are transmission electron micrographs of sections of monkey retina (R) and vitreous (V) in the region of the vitreous base from control (FIG. 10A) and chondroitinase ABC treated (FIG. 10B) monkey eyes. The collagen fibrils (arrowheads, FIG. 10A) normally associated with the vitreous body are readily apparent in FIG. 10A, but are not apparent in the eye in which the vitreous body was disinserted (FIG. 10B). It should be noted that the vitreous body proper disinserts cleanly from the internal limiting membrane (arrows, both FIGS. 10A and 10B), leaving the internal limiting membrane intact.
Figure 10B:
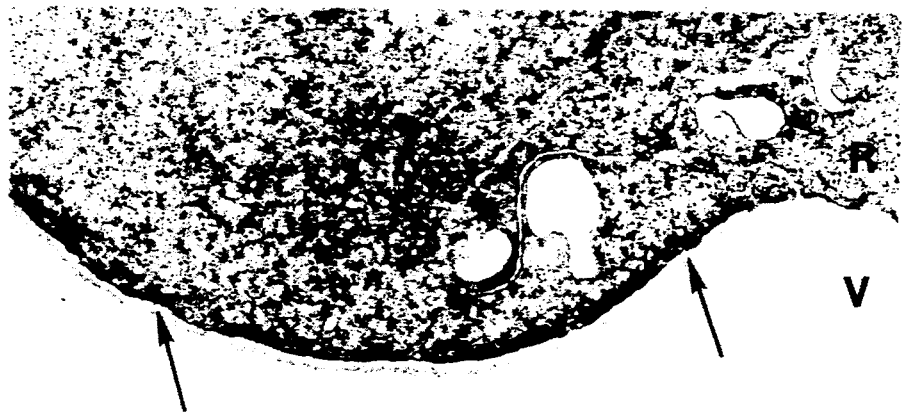
Figure 11:
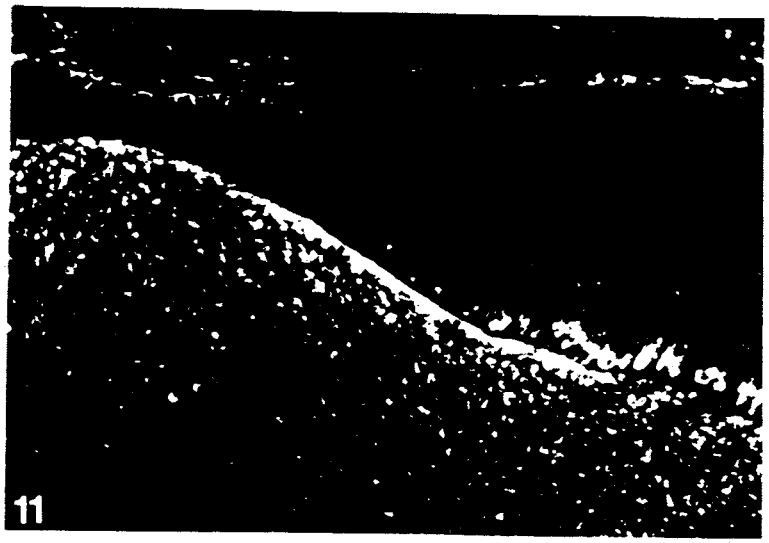
FIG. 11 is a fluorescence light micrograph depicting a section of retina from a seventeen-week old fetus following incubation of anti-chondroitin sulfate antibody. Intense binding of anti-chondroitin sulfate is observed within the vitreous base, even at this early stage of human development.
Figure 12:
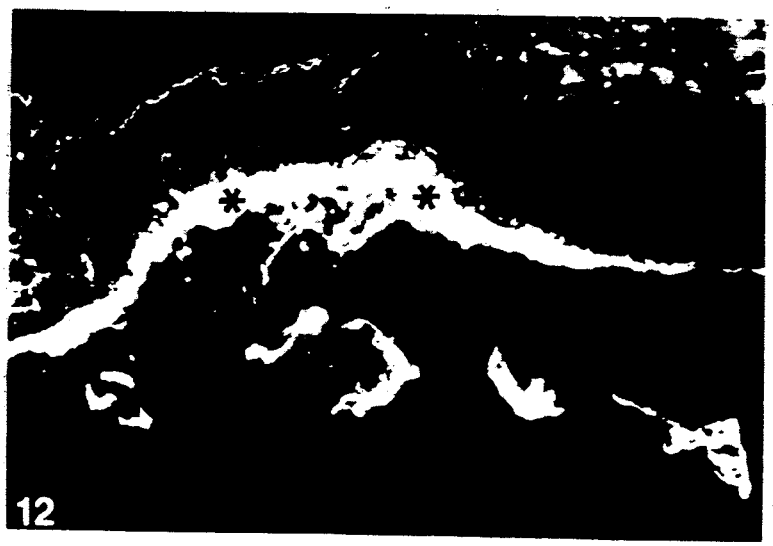
FIG. 12 is a fluorescence light micrograph of a section of adult human retina in the region of the vitreous base following incubation with anti-chondroitin sulfate antibody. Note the intense immunolocalization of chondroitin sulfate within the vitreous base and that the binding intensity decreases just posterior to the ora serata.
Figure 13:
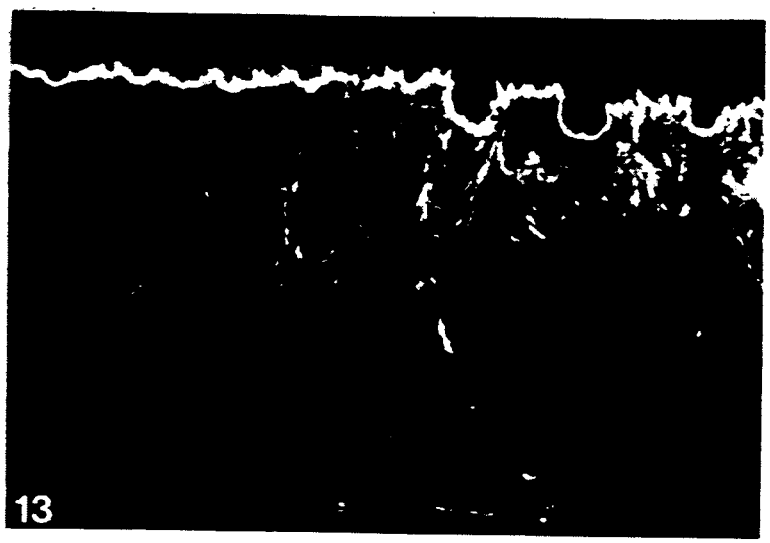
FIG. 13 is a fluorescence light micrograph depicting binding of anti-chondroitin sulfate antibody to the vitreous base associated with the pars plana of the dog retina demonstrating that the association of chondroitin sulfate proteoglycan with sites of firm vitreoretinal adhesion occurs in all mammalian species observed (porcine, bovine, ovine, rat, rabbit, monkey, human)
Figure 14:
FIG. 14 is a fluorescence light micrograph depicting binding of anti-chondroitin sulfate antibody to the vitreous associated with the posterior aspect of the lens capsule in the monkey.

In addition to the studies described hereinafter, other studies were performed in dog and autopsy human eyes. In both species, as in the monkey, chondroitin sulfate appears to be localized specifically within the vitreous base and other regions of firm vitreoretinal adhesion (see FIGS. 9-11). Further studies were performed in monkey and human autopsy eyes, with wedges of enucleated eyes being incubated in Ringer's solution containing either chondroitinase AC, chondroitinase ABC, or chondroitin 6-sulfatase. Each of these enzymes abrogated binding of anti-chondroitin sulfate antibody to the vitreous base and achieved complete disinsertion.

An additional set of experiments was conducted towards determining whether anti-chondroitin sulfate immunoreactivity is present between the retina and devastating epiretinal membranes which develop in various pathologies. In one monkey with epiretinal membranes (FIG. 7) and in a number of humans with proliferative vitreoretinopathy (PVR) or epiretinal membranes, intense binding of anti-chondroitin sulfate antibody was observed between the membranes and the retina. These results suggest that chondroitin sulfate may mediate adhesion between the retina and epiretinal membranes. The ability to disrupt this adhesion through the practice of the present invention may alleviate the severe complications currently associated with surgical removal of these membranes.

The following examples illustrate the practice of the invention.

EXAMPLE 1

Human, monkey, and porcine eyecups were fixed by immersion for one to four hours in freshly prepared 4.0% formaldehyde in 100 millimolar sodium cacodylate buffer (pH 7.4). The eyecups were trimmed, rinsed for a minimum of six hours in cacodylate buffer, embedded in acrylamide according to the protocol of Johnson and Blanks (Current Eye Res. 3:969-974, 1984) and sectioned on a cryostat at $-20°$ C. In some instances, tissues were embedded directly in acrylamide or O.C.T. embedding media without fixation. For one micron thick sections, eyecups were fixed with 4.0% formaldehyde and stored for one to four weeks in cacodylate buffer containing 2.0% formaldehyde and 3.0% sucrose. Pieces of retina were infiltrated with 23 molar sucrose, mounted in Tissue Tek O.C.T. embedding media, rapidly frozen in liquid nitrogen and sectioned on an ultramicrotome with a cryosectioning attachment.

Sections were exposed to a variety of monoclonal antibodies directed against chondroitin sulfate glycosaminoglycans or proteoglycans for one to two hours at room temperature in a humidified environment, rinsed extensively in phosphate buffered saline, and subsequently exposed to fluoresene-conjugated goat anti-mouse IgG or IgM, as appropriate, for thirty to sixty minutes under similar conditions, rerinsed and examined by epifluorescence microscopy on an Olympus Vanox microscope. Photographs were made on Kodak Tri-X film using an exposure index of 800.

The results of these studies demonstrated that anti-chondroitin sulfate antibodies bind intensely to the vitreous base and the peripapillary region in all species examined (see FIGS. 1-13). The distribution of chondroitin sulfate antibody binding corresponds directly to those regions of the vitreoretinal interface which are known to be the regions of firmest adhesion between these two tissues, and chondroitin sulfate is thus identified as present in regions of the strongest vitreoretinal adhesion.

EXAMPLE 2

In order to further confirm that chondroitin sulfate is involved in vitreoretinal adhesion, standard vitrectomies were performed on the right eyes of three monkeys of various ages to test whether the chondroitin sulfate-binding regions described above were removed during vitrectomy. The left eyes of these animals were utilized as controls. The results of these studies indicated that the vitreous base and other regions of normal vitreoretinal adhesion and their associated regions of strong anti-chondroitin sulfate-binding were not removed during standard vitrectomy, even in cases where a concerted effort was made to remove the vitreous base (see FIG. 3).

EXAMPLE 3

An experiment was conducted to determine whether or not regions of strong vitreoretinal adhesivity which are normally not removed by standard vitrectomy could be removed by injecting protease-free chondroitinase ABC into an eye. This enzyme was injected into the right eye of one monkey following a standard vitrectomy. The enzyme-containing solution was left in place for 20 minutes prior to vitreous lavage and enucleation. The eye was prepared for light immunocytochemistry using anti-chondroitin sulfate antibodies as well as for electron microscopy; the left eye was used as a control. Based on conventional histology and immunocytochemistry, the results indicated that the chondroitin sulfate immunoreactivity was completely abrogated and the vitreous base completely disinserted or removed (see FIG. 4). Further, no signs of retinal or ciliary body toxicity were noted by light or electron microscopy.

EXAMPLE 4

Studies were conducted to establish the maximal and minimal effective doses of protease-free chondroitinase ABC required to disinsert completely the vitreous base and other regions of the vitreous body from the ciliary epithelium and neural retina one hour following an intravitreal injection of the enzyme. Procedures were performed on four cynomologus monkeys between four and eight years of age, healthy and without any ocular complications. In all cases, eyes were examined both funduscopically and ultrasonically both prior to and following the enzymatic procedure.

Animals were anesthetized and approximately 400 to 600 $\mu$l of core vitreous removed using standard vitrectomy procedures. The removed volume of vitreous in each of the four monkeys was exchanged with sterile, balanced salt solution containing 25U, 100U, 110U, 150U, and 240U of protease-free chondroitinase ABC and 0.03M sodium acetate. In all cases, formed vitreous was observed within the experimental eyes of each monkey through the operating microscope. The animals were kept on anesthesia for one hour, the head being turned from side to side every 15 minutes in order to prevent pooling of the injected enzyme and to allow exposure of the peripheral vitreous to the enzyme. Following one hour of enzyme exposure, both the experimental and control eyes were again examined by ultrasonography. Immediately following this procedure, the animals were sacrificed and both eyes enucleated and bisected. One-half of each eye was fixed in 4% paraformaldehyde for routine histology/pathology and the other half of each eye was fixed in one-half strength Karnovsky's fixative for observation using conventional transmission electron microscopy. The portion of each eye fixed in 4% paraformaldehyde was used for routine histological observation of putative deleterious effects of enzyme treatment on ocular tissues. In all cases, the right eye served as a control eye and was processed identically to the experimental eye.

Based upon gross examination, funduscopy, sonography, routine histology/pathology, immunocytochemistry and conventional transmission electron microscopy, the results may be summarized as follows:

1. In the monkey receiving 25U chondroitinase ABC for a treatment period of one hour, the vitreous body was partially disinserted. Grossly, some vitreous in the region of the vitreous base could still be grasped by forceps. The fact that vitreous remained was further documented by routine histological stains, anti-chondroitin sulfate antibodies, and transmission electron microscopy. No other effects of enzyme treatment were noted in the eye; the retina, retinal pigmented epithelium, optic nerve head, ciliary epithelium, lens, and cornea all appeared normal following the above-described procedure.

2. In the monkeys treated with 100, 150U, and 240U of protease-free chondroitinase ABC, the vitreous body was completely disinserted after one hour. It was not possible to grasp the dense accumulation of vitreous which is normally present at the vitreous base and vitreous-associated molecules and structures could not be detected by routine histological observation, anti-chondroitin sulfate antibodies or transmission electron microscopy. All other ocular structures appeared normal in these two eyes.

EXAMPLE 5

Example 4 was repeated with five cynomologus monkeys being used, with the monkeys receiving 10, 20, 50, and 100U of protease-free chondroitinase ABC. The same procedures as in Example 4 were employed except for the following modifications. The balanced salt solution used for infusion was prewarmed to 37° C. and adjusted to 0.03M sodium acetate. In one experiment, the protease-free chondroitinase ABC was diluted in balanced salt solution rather than Tris acetate buffer with no differences in results being noted. Vitreous samples were collected prior to and following enzymatic disinsertion. The proteins in these fractions were separated by SDS-polyacrylamide gel electrophoresis to compare protein profiles before and after the disinsertion procedure. In one eye, the enzyme was introduced via a gas-fluid exchange technique to investigate other methods of enzyme delivery. The head was turned more often than in Example 4 to insure that the vitreous contents were continually agitated. The purity of chondroitinase ABC was tested by SDS-polyacrylamide gel electrophoresis and protein hydrolysis; no evidence of protease activity was noted in the enzymes utilized.

Based on gross examination, funduscopy, sonography, routine histology/pathology, immunocytochemistry and conventional transmission electron microscopy, the results may be summarized as follows:

1. In the monkeys receiving 10U, 20U, and 50U chondroitinase ABC, the vitreous was not completely disinserted. However, in all cases, the posterior vitreous and the anterior hyaloid were detached from the posterior retinal and posterior lens surface, respectively. However, the vitreous remained attached to some regions of the vitreous base. No other effects of enzyme treatment were noted in these eyes; the retina, retinal pigmented epithelium, optic nerve head, ciliary epithelium, lens, iris, and cornea all appeared normal following procedures in these animals.

2. Two monkeys were treated with 100U of protease-free chondroitinase ABC. In one of these animals, the vitreous body was completely disinserted after one hour of treatment and, in the other monkey, it was not. The latter was probably due to an attempt to filter the enzyme prior to its injection into the eye and not to an inability of this dosage to disinsert the vitreous. In the other eye, the vitreous was disinserted, vitreous-associated molecules and structures could not be detected by routine histological observation, by anti-chondroitin sulfate antibodies, or by transmission electron microscopy. All other ocular structures appeared normal in these eyes.

EXAMPLE 6

The procedures of Examples 4 and 5 were repeated with the administration of 200U of protease-free chondroitinase ABC for treatment periods of 10, 15, 20, 30, and 45 minutes with the following results.

For a treatment period of 10 minutes, the vitreous was not disinserted, and for a treatment period of 15 minutes, the vitreous was only partially disinserted.

For treatment periods of 20, 30, and 45 minutes, the vitreous was completely disinserted.

EXAMPLE 7

The procedures of Examples 4 and 5 were repeated with the administration of 75U of protease-free chondroitinase ABC for a treatment period of 2 hours resulting in complete disinsertion of the vitreous.

The administration of 20U of protease-containing chondroitinase ABC injected intravitreally following paracentesis resulted in lens dislocation, massive orbital edema, and retinal detachment.

EXAMPLE 8

The Procedures of Examples 4 and 5 were repeated with the administration of 40U of $\beta$-glucuronidase to post mortem wedges for a treatment period of 30 minutes resulting in partial disinsertion of the vitreous.

The administration of 25U each of cathepsins A, B, and D for a treatment period of 90 minutes resulted in no disinsertion of the vitreous.

The administration of 40U each of heparitinase I and II to post mortem wedges for a treatment period of 30 minutes resulted in partial disinsertion of the vitreous.

In view of the above, it will be seen that the several objects of the invention are achieved and other advantageous results attained.

As various changes could be made in the above methods without departing from the scope of the invention, it is intended that all matter contained in the above description or shown in the accompanying drawings shall be interpreted as illustrative and not in a limiting sense.

What is claimed is:

1. A method for selectively and completely disinserting the ocular vitreous body, epiretinal membranes or fibrocellular membranes from the neural retina, ciliary epithelium and posterior lens surface of the mammalian eye as an adjunct to vitrectomy which comprises administering to said eye an effective amount of an enzyme which disrupts or degrades chondroitin sulfate proteoglycan localized specifically to sites of vitreoretinal adhesion and thereby permit complete disinsertion of said vitreous body and/or epiretinal membranes.

2. A method as set forth in claim 1 wherein said enzyme is a protease-free glycosaminoglycanase.

3. A method as set forth in claim 2 wherein said enzyme is selected from the group consisting of protease-free chondroitinase ABC, chondroitinase AC, chondroitinase B, chondroitin 4-sulfatase, chondroitin 6-sulfatase, hyaluronidase, and $\beta$-glucuronidase.

4. A method as set forth in claim 1 wherein said effective amount is between approximately 1 and 10,000 units of said enzyme.

5. A method as set forth in claim 1 wherein said effective amount is between approximately 50 and 1000 units of said enzyme.

6. A method as set forth in claim 1 wherein said enzyme is administered to said eye by means of intravitreal, subvitreal, sublenticular or posterior chamber administration.

7. A method as set forth in claim 1 wherein said enzyme is administered in the form of a pharmacologically acceptable buffered solution.

8. A method as set forth in claim 7 wherein said solution is buffered with sodium acetate.

9. A method as set forth in claim 3 wherein said enzyme is chondroitinase ABC

* * * * *